(12) United States Patent
Socransky

(10) Patent No.: US 12,427,330 B2
(45) Date of Patent: *Sep. 30, 2025

(54) SYSTEM AND METHOD FOR TRANSMITTING RADIO FREQUENCY ENERGY AT A VIRUS RESONANT FREQUENCY TO DISABLE IT

(71) Applicant: Alexander Socransky, Los Angeles, CA (US)

(72) Inventor: Alexander Socransky, Los Angeles, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/615,517

(22) Filed: Mar. 25, 2024

(65) Prior Publication Data
US 2024/0374907 A1  Nov. 14, 2024

Related U.S. Application Data

(63) Continuation of application No. 17/227,000, filed on Apr. 9, 2021, now Pat. No. 11,938,335.

(60) Provisional application No. 63/008,483, filed on Apr. 10, 2020.

(51) Int. Cl.
*A61N 1/40* (2006.01)

(52) U.S. Cl.
CPC .................................... *A61N 1/40* (2013.01)

(58) Field of Classification Search
None
See application file for complete search history.

(56) References Cited

U.S. PATENT DOCUMENTS 11,938,335 B2 *  3/2024  Socransky ............... A61N 1/40
2021/0299289 A1 *  9/2021  Raymond ................. A61L 2/12

\* cited by examiner

*Primary Examiner* — Mark W. Bockelman
(74) *Attorney, Agent, or Firm* — Olivo IP Law Group, P.C.; John W. Olivo, Jr.

(57) ABSTRACT

The invention relates to a method and system for treating an area with radio frequency radiation with a resonant frequency and modulation function calibrated to destroy harmful pathogens, such as bacteria, viruses or other germs. According to the present invention, transmitters are used to neutralize harmful pathogens within a space, and may be used with corresponding receivers are used to verify the functional performance of the transmitters, and to create a data stream so that human occupants of the spaces so being treated can be assured that the areas they occupy have been so treated.

23 Claims, 10 Drawing Sheets

SYSTEM AND METHOD FOR TRANSMITTING RADIO FREQUENCY ENERGY AT A VIRUS RESONANT FREQUENCY TO DISABLE IT

PRIORITY CLAIMS

This application is a continuation of U.S. patent application Ser. No. 17/227,000, filed Apr. 9, 2021, which claims the benefit of U.S. Provisional Patent Application Ser. No. 63/008,483, filed on Apr. 10, 2020, the contents of which are incorporated herein by reference.

BACKGROUND OF THE INVENTION

This invention relates to the process of finding a resonant frequency of a virus and then equipping various venues with suitable broadcast transmitters so that targeted areas are treated with radio frequency energy to eliminate virus buildup or disinfect areas either in high density or populated areas or even more secluded areas.

In the past few decades, tremendous efforts have been made to kill airborne viruses such as severe acute respiratory syndrome (SARS) coronavirus or influenza viruses, which have caused catastrophic illness worldwide. Current airborne virus epidemic prevention methods that can be recommended for public spaces include strong chemical inactivation, Ultraviolet (UV) irradiation and microwave thermal heating. All these methods may affect the general public in unhealthy ways if appropriate governmental and medical association limits are not properly adhered to. It has been demonstrated that ultrasonic energy can be absorbed by viruses, and that viruses can be inactivated by generating the viral corresponding resonance ultrasound vibrations, which are measured in gigahertz (GHz) wave frequencies.

It has been demonstrated that dipolar mode of the confined acoustic vibrations (CAVs) inside viruses can be resonantly excited by microwaves of the same frequency with a resonant microwave absorption effect. The observed microwave resonance absorption phenomenon indicates a possible structure-resonant energy transfer (SRET) effect from electromagnetic waves (EM waves) to CAVs of viruses. This SRET process is an efficient way to excite the vibrational mode of the whole virus structure due to a 100% energy conversion of a photon into a phonon of the same frequency, but the overall SRET efficiency is also related to the mechanical properties of the surrounding environment, which can influence the quality factor of the oscillator (virus). Again, accomplishing an analogous result from electromagnetic waves has not been focused upon.

The SRET directed from a microwave to a virus can be efficient enough so that airborne virus is inactivated with reasonable microwave power density that is safe for the open public. To investigate the SRET efficiency from EM waves to CAVs in viruses, a theoretical model has been developed to describe the relation between the induced stress and the field magnitude of the illuminating microwave. Since a virus can be inactivated when the induced stress fractures the structure of a virus, it becomes necessary to explore the SRET efficiency from microwaves to viruses by measuring the virus inactivation threshold. When observing the inactivation ratio of Influenza A virus subtype H3N2 (H3N2) virus at dipolar-mode-resonance and off-resonance microwave frequencies as well as with different microwave powers, quantitative plaque assay was then applied to calculate the titer of virus samples before and after the microwave illumination. These results indicate efficient SRET from microwave to viruses, which results in higher inactivation ratio of viruses at the dipolar resonant frequency. It is at that resonant frequency that the microwave power density threshold for H3N2 inactivation was found to be below public safety standards. The real-time reverse transcription polymerase chain reaction (real-time RT-PCR) method has confirmed that the main inactivation mechanism is through physically fracturing the viruses while the RNA genome was not degraded by the microwave illumination, supporting the findings that the SRET mechanism is fundamentally different from the microwave thermal heating effect. These results can be used to establish new epidemic prevention strategy in public spaces for an airborne virus. A major problem with all existing solutions is that the solution may be less healthy for humans than the cure. There exists a need to use modulated or unmodulated radio frequency propagation to kill germs, or any undesired bacteria or viruses, without harming humans.

SUMMARY OF THE INVENTION

The present invention pertains to a method and system for transmitting radio frequency energy at a virus's resonant frequency to disable it. A virus is known to resonate in the confined-acoustic dipolar mode with microwave of the same frequency. However, this effect has not been considered in previous virus-microwave interaction studies and microwave-based virus epidemic prevention. It has been shown that the structure-resonant energy transfer effect from microwaves to a virus can be efficient enough so that airborne virus is inactivated with reasonable microwave power density safe for the open public. Therefore, a theoretical model to estimate the microwave power threshold for virus inactivation was obtained. Such structure-resonant energy transfer induced inactivation is mainly through physically fracturing the virus structure, which has been confirmed by real-time reverse transcription polymerase chain reaction. These results provide a pathway toward establishing a new epidemic prevention strategy an airborne virus.

In one embodiment, the virions of influenza viruses are structurally spherical and comprised of genomes. The viral protein and genome have similar mechanical properties. For the estimation of dipolar vibration frequencies, the virion is treated as a homogenous sphere. A dipolar oscillation frequency of 8.4 GHz is shown to have a strong resonant effect on the virus inactivation ratio, thus indicating that the observed virus inactivation after microwave illumination is due to the proposed SRET from microwave to virus. This results in the structural fracture of the virus. Viral inactivation can be achieved using an illumination of 82 $W/m^2$, which is considered low enough that it can be used in public spaces. This demonstrates a sharp contrast to current methodologies, for example, including strong chemical inactivation, UV irradiation and microwave thermal heating with over 100 W microwave power, all of which are not safe for use in public spaces.

In another embodiment, the present invention operates by observing the structure resonance energy transfer from microwave to CAVs of a virus in water-based solution, the efficiency of such energy transfer has been determined through exploring the virus inactivation ratio. Based on a proposed damped mass-spring model and the experimentally measured microwave absorption cross-section of a single virus, threshold magnitude of electric field to fracture viruses at different illuminated frequencies can be estimated. Through microwave illumination, it has been shown through the use of a plaque assay experiment that the inactivation ratio reaches its maximum at the resonant frequency of the dipolar resonance. The main inactivation mechanism is able to physically fracture a virus without degrading the viral RNA genome. This demonstrates a new energy transfer mechanism between EM waves and viruses, and also indicates an efficient SRET effect. Therefore, a viral inactivation threshold is achieved using a microwave power density that is safe for use in public spaces.

Other features and aspects of the disclosed technology will become apparent from the following detailed description, taken in conjunction with the accompanying drawings, which illustrate, by way of example, the features in accordance with embodiments of the disclosed technology. The summary is not intended to limit the scope of any inventions described herein, which are defined solely by the claims attached hereto.

DETAILED DESCRIPTION OF THE PREFERRED EMBODIMENT

Figure 1:
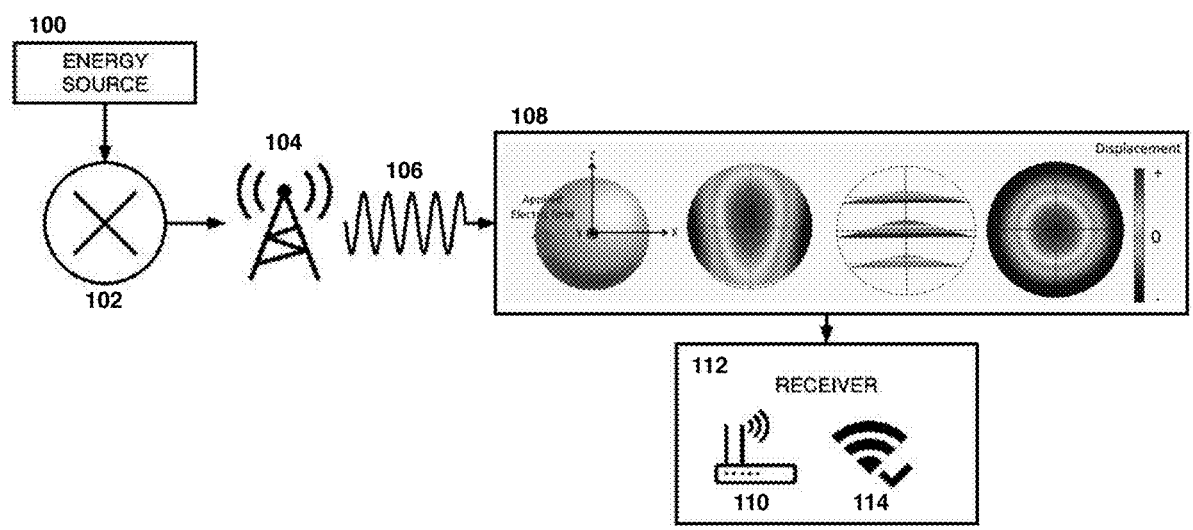
FIG. 1 is a schematic diagram of an energy source with modulation circuit and an antenna, and a status monitoring device with a receiver and corresponding antenna.

FIG. 1 is a schematic diagram of an energy source with modulation circuit and an antenna, and a status-monitoring device with a receiver and corresponding antenna. In FIG. 1, modulator 102, powered by an energy source 100, provides an electromagnetic signal to a broadcast antenna 104, where an electromagnetic wave 106 is propagated away from the antenna. Modulator or radio 104 may be a manual or remote controlled or software-controlled radio or transmitter, so that the energy transmitted is carefully calibrated to destroy the pathogens intended, while being healthy for other targets such as humans.

According to the present invention, a database of viruses or bacteria or other pathogens could be ascertained, and broadcast out to modulators 102. Modulators 102 transmit energy to form electromagnetic waves formulated to kill harmful viruses. In that manner, the system according to the present invention is updated as new harmful viruses present themselves. Samples of viruses or other harmful pathogens, as they are detected, are analyzed so that their destructive resonant frequency components are determined. Once it is determined that new harmful viruses or pathogens are in the public domain, the modulator 102 may receive signals from a database of harmful pathogens or viruses, so that the system may be updated periodically or continuously. In addition, multiple antennae may be disposed geographically or within any enclosed or defined space, so that the energy amplitude may be attenuated on a per antenna basis, so that energy is targeted and tuned for killing viruses and not harming other living organisms such as humans.

The wave 106 has both electronic and magnetic components, orthogonal to each other, and is a modulated wave with frequency components selected corresponding to viral loads or germs within the field of propagation. Specifically, the resonant frequencies of viruses or germs to be neutralized or disabled are selected so that modulator 102 may be so tuned. The wave 106 may be disposed throughout an area of propagation for virus or germ elimination 108. The wave frequency 106 is then transmitted to the receiving antenna 110 within the receiver unit 112, thereby monitoring the electromagnetic wave 106, so that the status of viral disablement may be confirmed, and in turn, communicated to an internet port 114. Once the status is output to the internet via port 114, various human occupants of a space corresponding to areas that have been sanitized by wave 106 may use a smartphone with application software so that occupants have status as to whether an area is safe or not in terms of viruses or germs. The receiving unit 112 can adjust the output of the transmitting antenna to push the range of covered space as long as its within acceptable limits, and can be adjusted to give less coverage if necessary, through the use of over the air adjustments to modulator 102.

Figure 2:
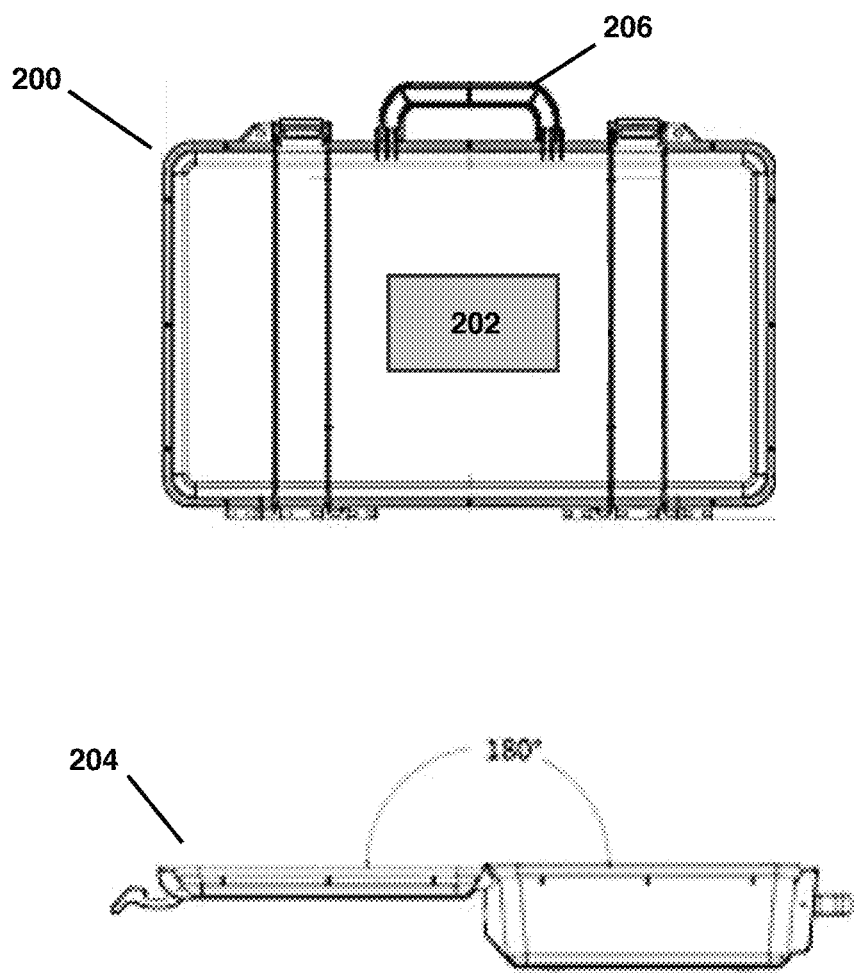
FIG. 2 is a diagram of a local sterilization chamber for small object anti-viral neutralization.

FIG. 2 is a diagram of a local portable sterilization chamber for small object anti-viral neutralization. In accordance with the preferred embodiment of the present invention, FIG. 200 is a small, portable chamber or case that is equipped with a battery powered anti-viral neutralization device 202. An object can be placed into the case 200, through a hatch or door 204 that, when closed, can transmit electromagnetic waves to neutralize viral pathogens on the surface of the object. The case 200 is fitted with a handle 206 to facilitate transportation.

Figure 3:
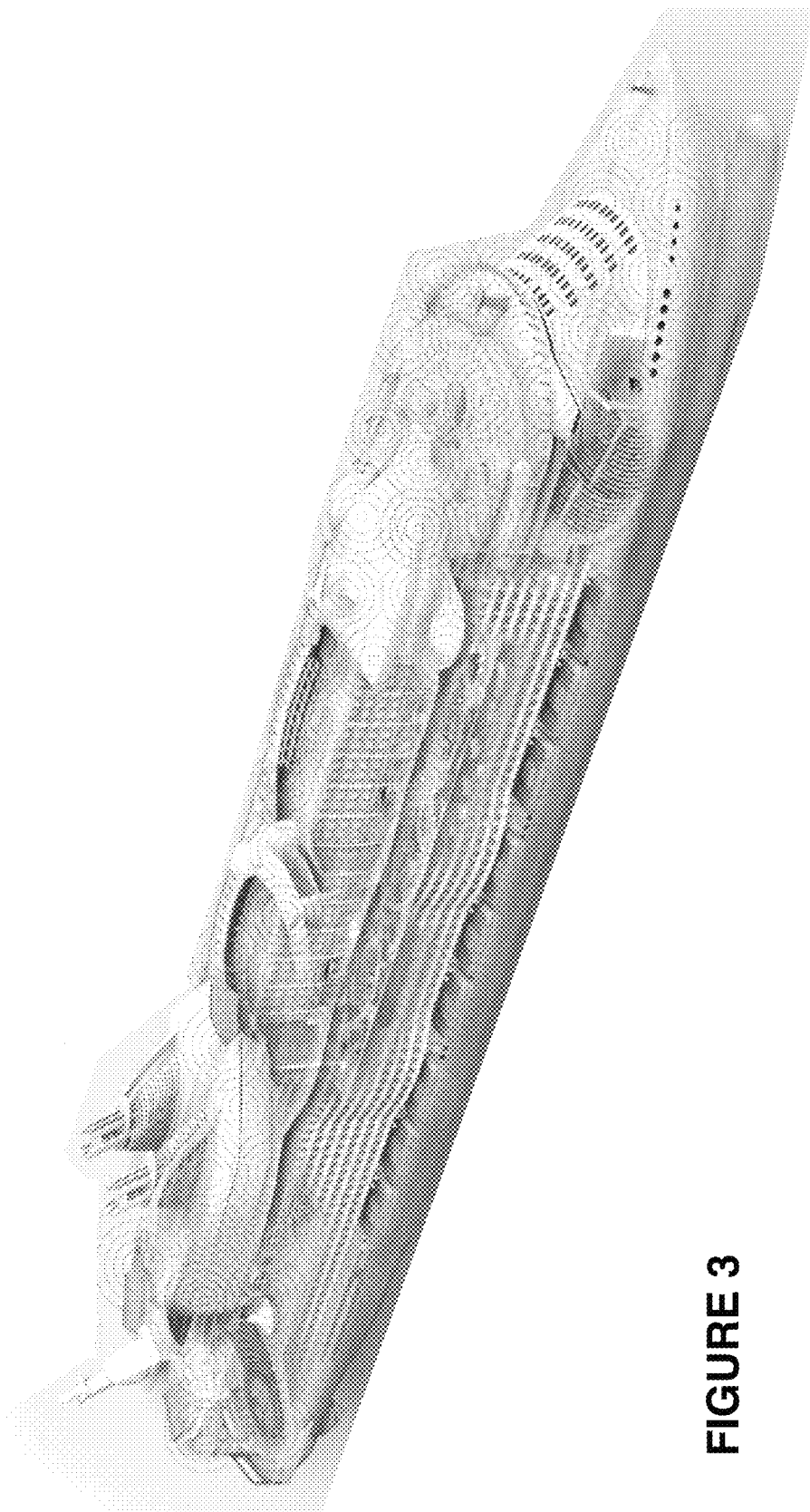
FIG. 3 is a diagram of a maritime chamber for anti-viral neutralization.

FIG. 3 is a diagram of a maritime chamber for anti-viral neutralization. In accordance with the preferred embodiment of the present invention, a large maritime vessel, such as a cruise ship, as shown in FIG. 3, can be equipped with a multitude of localized anti-viral neutralization devices that can cover all areas aboard the ship. Each anti-viral neutralization device can be strategically placed so as to overlap with the adjacent devices in terms of covering a range of open space.

Figure 4:
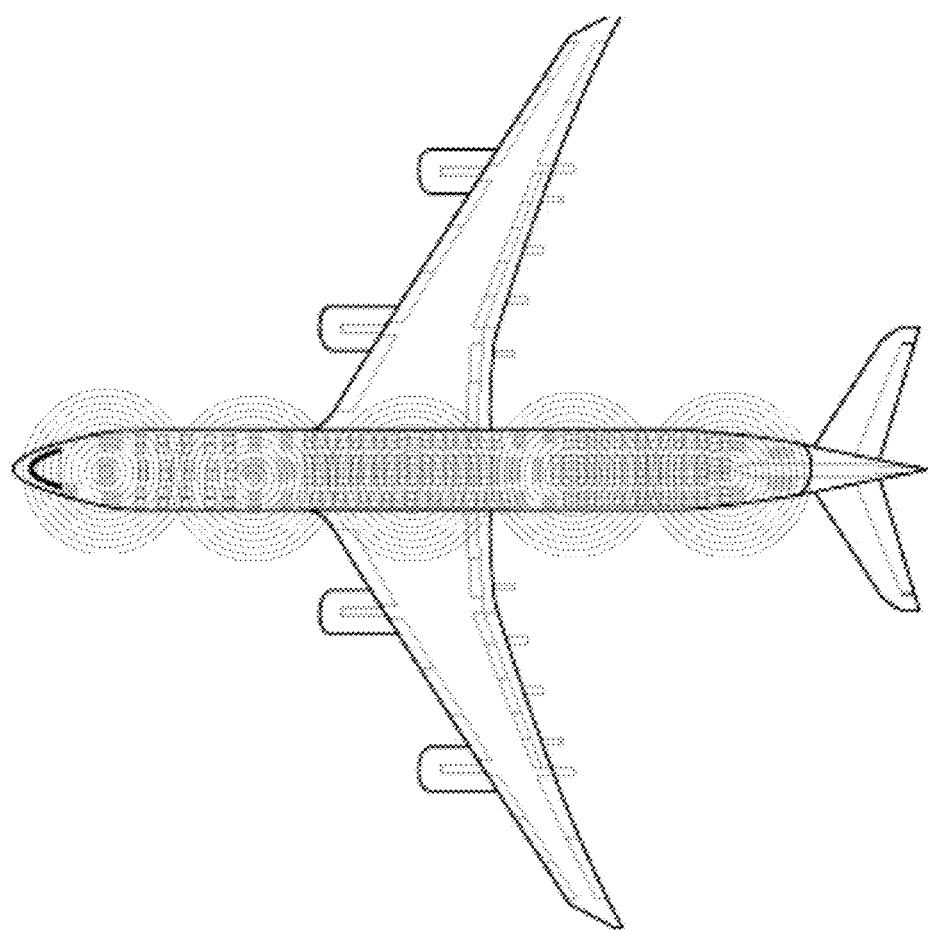
FIG. 4 is a diagram of an airplane chamber for anti-viral neutralization.

FIG. 4 is a diagram of an airplane chamber for anti-viral neutralization. In accordance with the preferred embodiment of the present invention, a commercial airplane, as shown in FIG. 4, can have several anti-viral neutralization devices placed so that all public space within the aircraft is covered by the range of each device.

Figure 5:
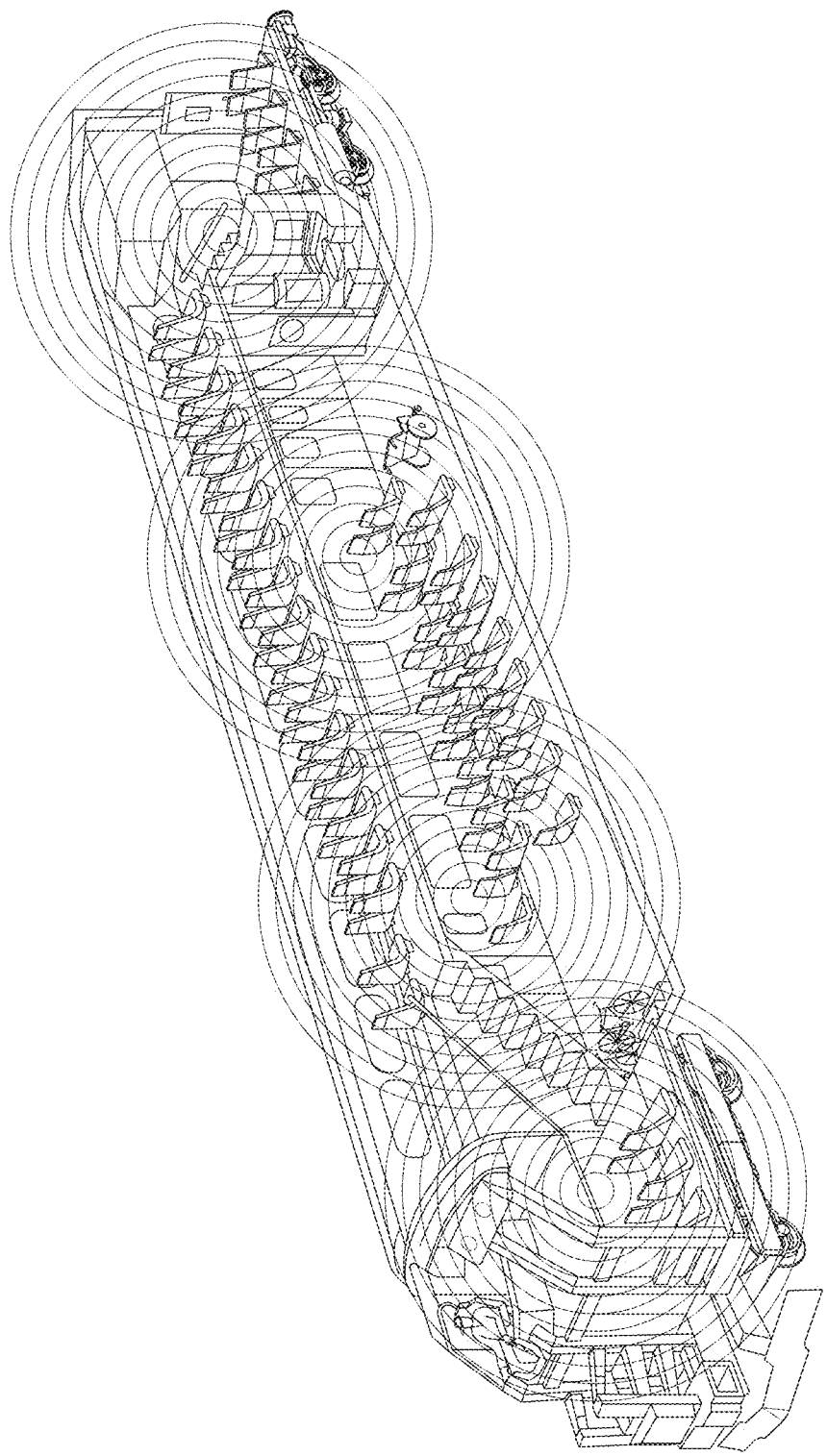
FIG. 5 is a diagram of a train chamber for anti-viral neutralization.

FIG. 5 is a diagram of a train chamber for anti-viral neutralization. In accordance with the preferred embodiment of the present invention, a commuter train car, as shown in FIG. 5, can have several anti-viral neutralization devices placed so that the range of each device can adequately cover the space of the entire train car.

Figure 6:
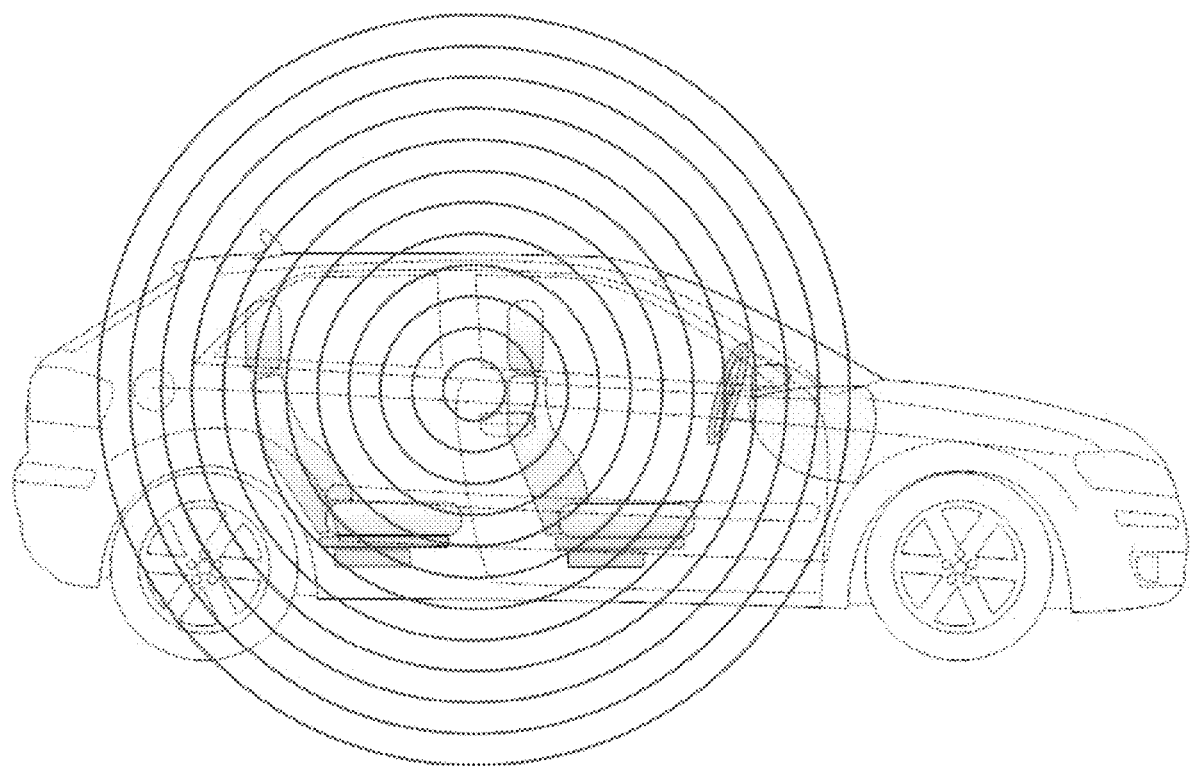
FIG. 6 is a diagram of an automobile chamber for anti-viral neutralization.

FIG. 6 is a diagram of an automobile chamber for anti-viral neutralization. In accordance with the preferred embodiment of the present invention, an automobile can be fitted with at least one anti-viral neutralization device in the center of the vehicle (such as a center console) so that the range of anti-viral neutralization can cover the entire vehicle interior.

Figure 7:
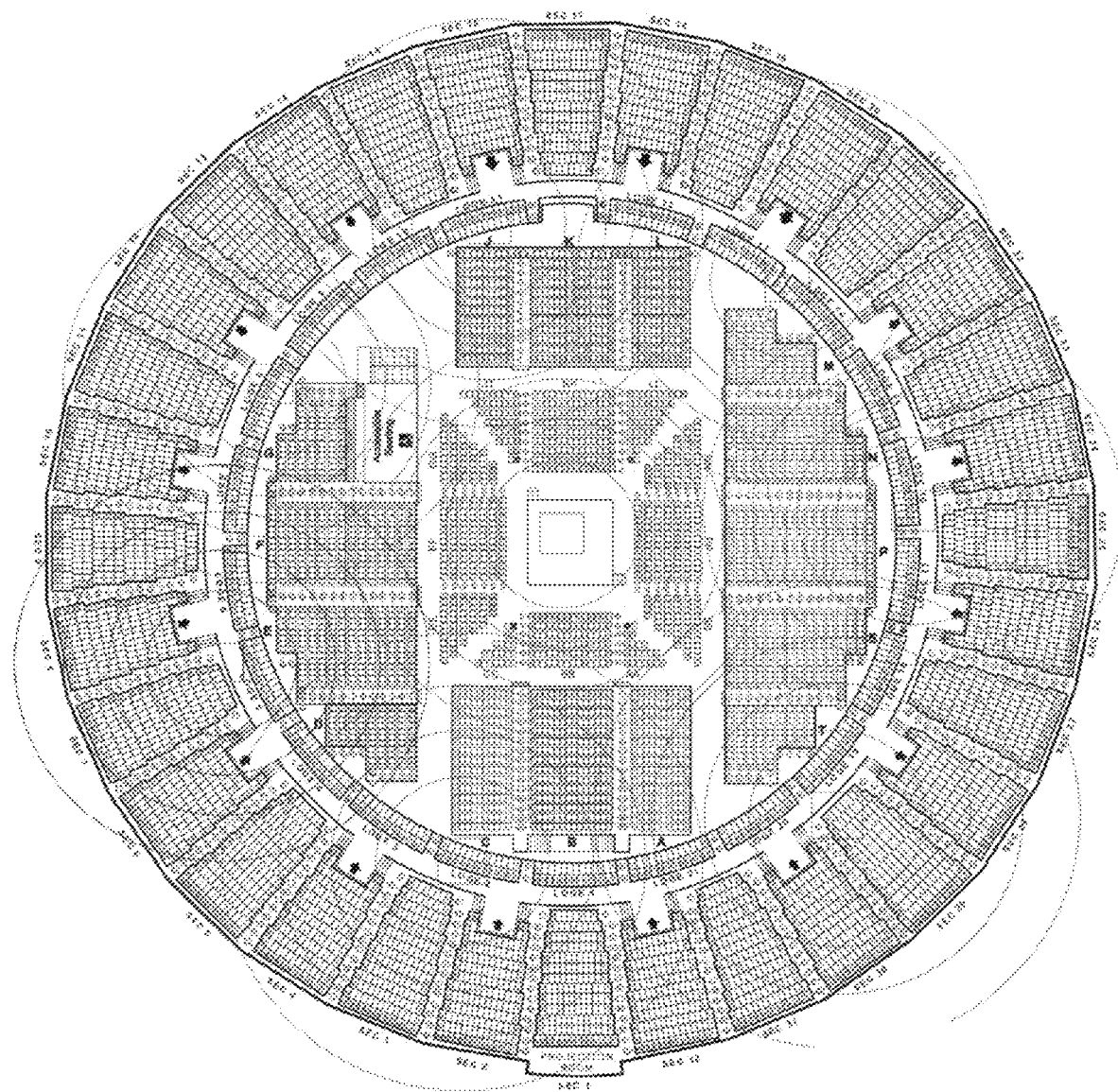
FIG. 7 is a diagram of a large-scale venue for anti-viral neutralization.

FIG. 7 is a diagram of a large-scale venue for anti-viral neutralization. In accordance with the preferred embodiment of the present invention, a large-scale venue, such as a stadium, as shown in FIG. 7, can be equipped with a multitude of localized anti-viral neutralization devices that can cover the entire area of the stadium. Each anti-viral neutralization device can be strategically placed so as to overlap with the adjacent devices in terms of covering a range of open space.

Figure 8:
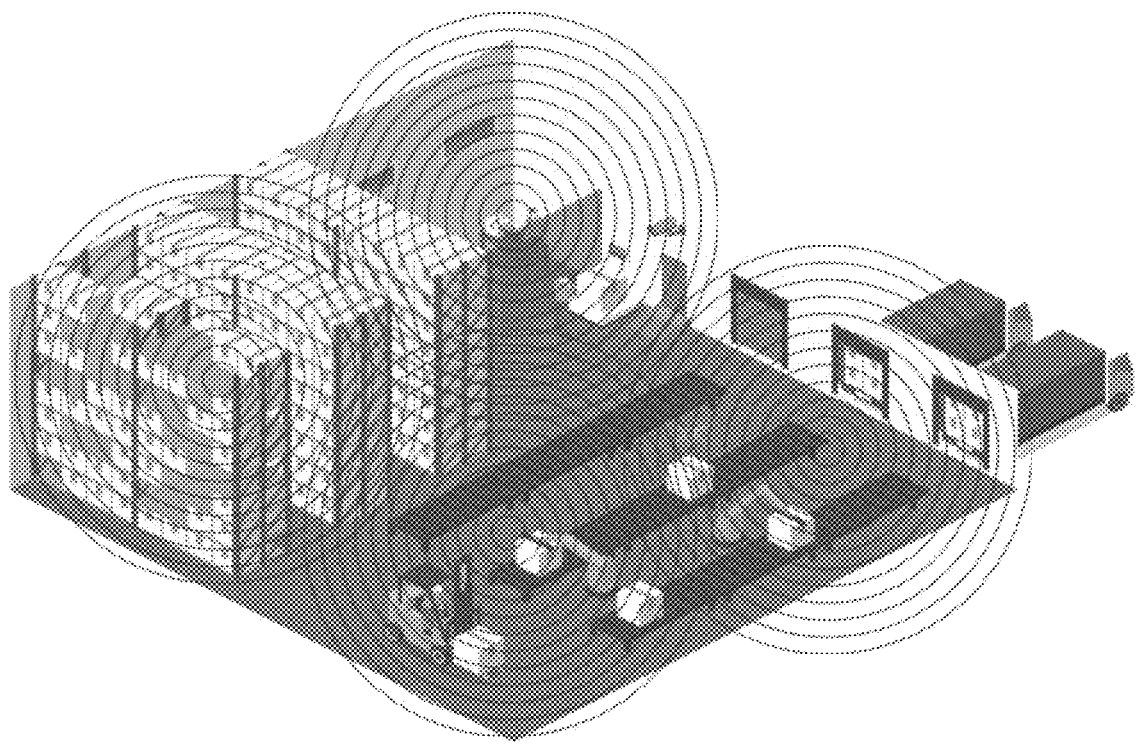
FIG. 8 is a diagram of a commercial venue for anti-viral neutralization.
Figure 9:
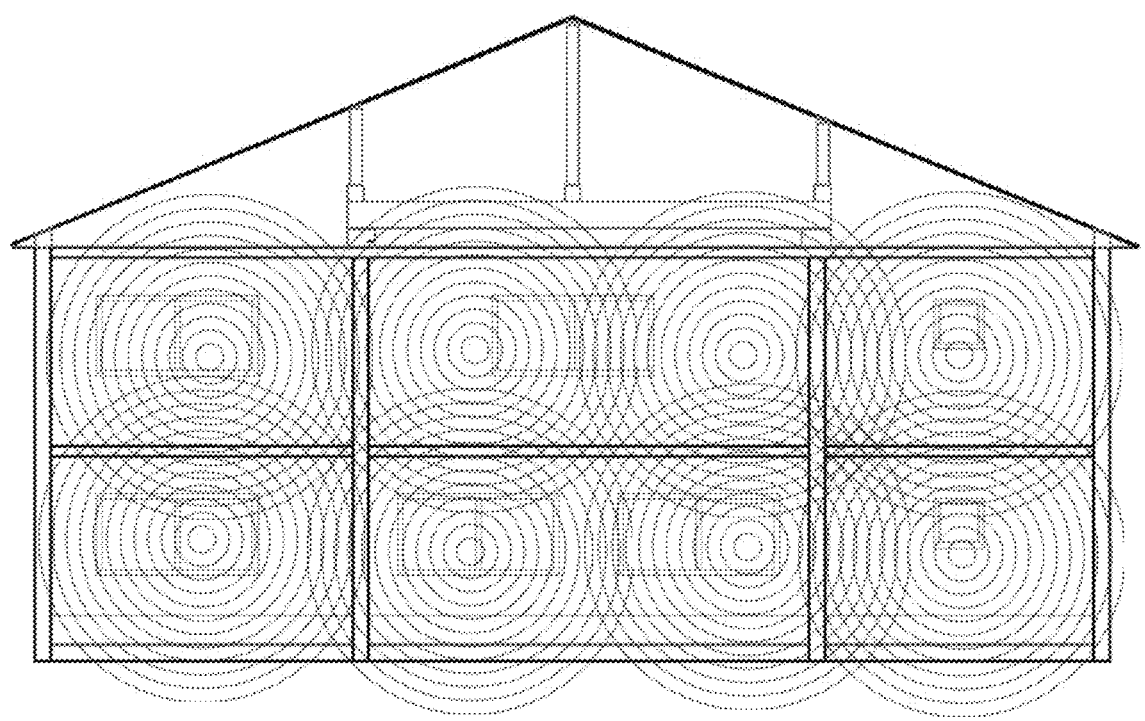
FIG. 9 is a diagram of a residential structure for anti-viral neutralization.
Figure 10:
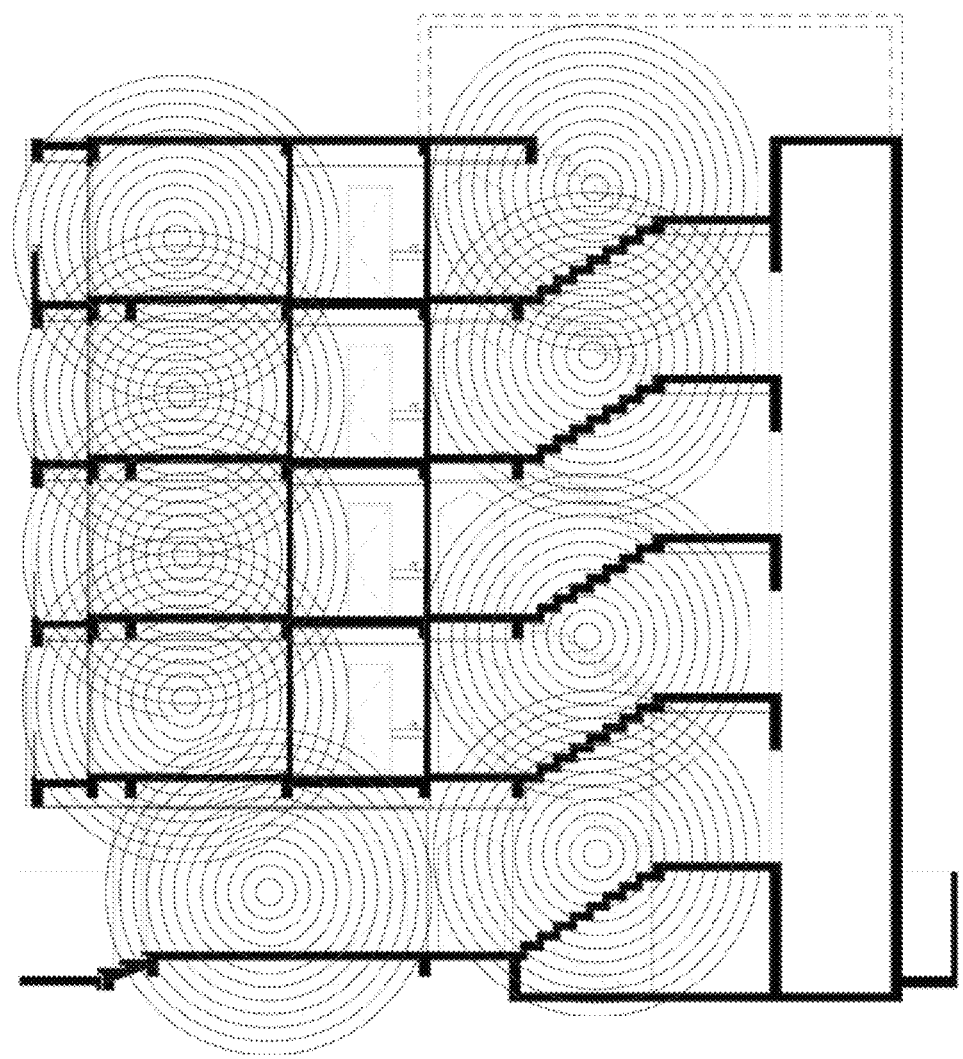
FIG. 10 is a diagram of a dense residential structure for anti-viral neutralization.

FIG. 8 is a diagram of a commercial venue for anti-viral neutralization. In accordance with the preferred embodiment of the present invention, a commercial venue, such as a large warehouse, as shown in FIG. 8, can have several anti-viral neutralization devices placed so that all public space within the warehouse is adequately covered by the range of each device.

FIG. 9 is a diagram of a residential structure for anti-viral neutralization. In accordance with the preferred embodiment of the present invention, a residential structure, such as a house, as shown in FIG. 9, can have several anti-viral neutralization devices placed so that the range of each device can adequately cover the space of the entire interior area of the home.

FIG. 10 is a diagram of a dense residential structure for anti-viral neutralization. In accordance with the preferred embodiment of the present invention, a dense residential structure, such as an apartment building, as shown in FIG. 10, can have several anti-viral neutralization devices placed so that the range of each device can adequately cover the space of each public area of the building. This includes placement of a device on every floor common area of the building, placement within the elevator shaft, and at least one anti-viral neutralization device inside every apartment or unit.

While various embodiments of the disclosed technology have been described above, it should be understood that they have been presented by way of example only, and not of limitation. Likewise, the various diagrams may depict an example architectural or other configuration for the disclosed technology, which is done to aid in understanding the features and functionality that may be included in the disclosed technology. The disclosed technology is not restricted to the illustrated example architectures or configurations, but the desired features may be implemented using a variety of alternative architectures and configurations. Indeed, it will be apparent to one of skill in the art how alternative functional, logical or physical partitioning and configurations may be implemented to implement the desired features of the technology disclosed herein. Also, a multitude of different constituent module names other than those depicted herein may be applied to the various partitions. Additionally, with regard to flow diagrams, operational descriptions and method claims, the order in which the steps are presented herein shall not mandate that various embodiments be implemented to perform the recited functionality in the same order unless the context dictates otherwise.

Although the disclosed technology is described above in terms of various exemplary embodiments and implementations, it should be understood that the various features, aspects and functionality described in one or more of the individual embodiments are not limited in their applicability to the particular embodiment with which they are described, but instead may be applied, alone or in various combinations, to one or more of the other embodiments of the disclosed technology, whether or not such embodiments are described and whether or not such features are presented as being a part of a described embodiment. Thus, the breadth and scope of the technology disclosed herein should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, may be combined in a single package or separately maintained and can further be distributed in multiple groupings or packages or across multiple locations.

Additionally, the various embodiments set forth herein are described in terms of exemplary block diagrams, flow charts and other illustrations. As will become apparent to one of ordinary skill in the art after reading this document, the illustrated embodiments and their various alternatives may be implemented without confinement to the illustrated examples. For example, block diagrams and their accompanying description should not be construed as mandating a particular architecture or configuration.

What is claimed is:

1. A system for transmitting energy to disable an organic pathogen so that organic pathogen efficacy is reduced and wherein said energy is used to fracture said organic pathogen structure, wherein said system comprises:

at least one database comprising virus, bacteria, and other pathogen data;

at least one energy source comprising a modulation circuit, an antenna, and a status-monitoring device;

at least one modulator or radio; and at least one portable sterilization chamber.

2. A system according to claim 1, wherein said energy is transmitted from a movable cart used inside a vehicle.

3. A system according to claim 1 wherein said energy having a resonant frequency that is modulated corresponding to said organic pathogen structure to obtain maximum efficacy.

4. A system according to claim 3 wherein said modulated frequencies are set to particular center frequencies corresponding to a targeted organic pathogen for reduction of presence of said organic pathogen.

5. A method for transmitting radio energy at an organic pathogen's resonant frequency to disable said organic pathogen including a structured resonant energy transfer effect so that airborne effects of said organic pathogen are eliminated and wherein said radio energy is used to fracture said organic pathogen structure, wherein said method comprises:
- accessing at least one database comprising organic pathogen and other pathogen data;
- transmitting said radio energy formulated to kill harmful organic pathogens via at least one anti-viral neutralization device comprising an energy source, a modulation circuit and an antenna, wherein said at least one anti-viral neutralization device is disposed upon a vehicle location within a vehicle; and
- monitoring said radio energy and a status of said organic pathogens via at least one status-monitoring device in communication with said at least one anti-pathogen neutralization device, wherein said at least one status-monitoring device comprises a receiver and a corresponding antenna.

6. A method according to claim 5 wherein said energy is transmitted from a movable cart used inside said vehicle.

7. A method according to claim 5 wherein said resonant frequency is modulated corresponding to said organic pathogen structure to obtain maximum efficacy.

8. A method according to claim 7 wherein said modulated frequencies are set to particular center frequencies corresponding to a targeted organic pathogen for reduction of presence of said organic pathogen.

9. A method of claim 5, wherein said at least one anti-viral neutralization device is updated as new organic pathogens are detected in a surrounding area.

10. A method of claim 5, wherein a plurality of antennas are disposed geographically to tune said radio energy.

11. A method of claim 5, wherein said receiver of said status-monitoring device receives at least one wave frequency that confirms a status of organic pathogen-disablement.

12. A method for transmitting radio energy at an organic pathogen's resonant frequency to disable said organic pathogen including a structured resonant energy transfer effect so that airborne effects of said organic pathogen are eliminated and wherein said radio energy is used to fracture said organic pathogen structure, wherein said method comprises:
- accessing at least one database comprising organic pathogen and other pathogen data;
- transmitting said radio energy formulated to kill harmful organic pathogens via at least one anti-viral neutralization device comprising an energy source, a modulation circuit and an antenna;
- monitoring said radio energy and a status of said organic pathogens via at least one status-monitoring device in communication with said at least one anti-organic pathogen neutralization device, wherein said at least one status-monitoring device comprises a receiver and a corresponding antenna; and
- deploying said anti-organic pathogen neutralization device within a location to be sterilized.

13. A method of claim 12, wherein said at least one anti-organic pathogen neutralization device is disposed on at least one cart on or within at least one vehicle aircraft for sanitation purposes.

14. A method of claim 12, wherein said at least one anti-organic pathogen neutralization device is updated as new organic pathogens are detected in a surrounding area.

15. A method of claim 12, wherein a plurality of antennas are disposed locationally to tune said radio energy.

16. A method of claim 12, wherein said receiver of said status-monitoring device receives at least one wave frequency that confirms a status of organic pathogen disablement.

17. A method of claim 12, wherein said at least one anti-organic pathogen-neutralization device is transported on at least one maritime vessel for sanitation purposes.

18. A method of claim 12, wherein said at least one anti-organic pathogen neutralization device is transported on at least one rail vehicle for sanitation purposes.

19. A method of claim 12, wherein said at least one anti-organic pathogen neutralization device is transported on at least one automobile for sanitation purposes.

20. A method of claim 12, wherein said at least one anti-organic pathogen neutralization device is deployed within a large-scale venue for sanitation purposes.

21. A method of claim 12, wherein said at least one anti-organic pathogen neutralization device is deployed within a residential structure for sanitation purposes.

22. A method of claim 12, wherein said at least one anti-organic pathogen neutralization device is deployed within a dense residential structure for sanitation purposes.

23. A method of claim 12, wherein said at least one anti-organic pathogen neutralization device is deployed within a commercial venue for sanitation purposes.

* * * * *